United States Patent
Chandler

(10) Patent No.: US 7,047,138 B2
(45) Date of Patent: May 16, 2006

(54) ZERO DEAD TIME ARCHITECTURE AND METHOD FOR FLOW CYTOMETER

(75) Inventor: Van S. Chandler, Austin, TX (US)

(73) Assignee: Luminex Corporation, Austin, TX (US)

( * ) Notice: Subject to any disclaimer, the term of this patent is extended or adjusted under 35 U.S.C. 154(b) by 45 days.

(21) Appl. No.: 10/694,086

(22) Filed: Oct. 28, 2003

(65) Prior Publication Data

US 2004/0098231 A1    May 20, 2004

Related U.S. Application Data

(63) Continuation of application No. 10/140,943, filed on May 9, 2002, now Pat. No. 6,658,357, which is a continuation of application No. 09/310,755, filed on May 13, 1999, now Pat. No. 6,411,904.

(60) Provisional application No. 60/085,415, filed on May 14, 1998, provisional application No. 60/085,381, filed on May 14, 1998.

(51) Int. Cl.
G01N 33/48 (2006.01)
G01N 33/50 (2006.01)
G06F 19/00 (2006.01)

(52) U.S. Cl. .................... 702/21; 702/19; 702/80; 700/72

(58) Field of Classification Search ........... 702/19–22, 702/30–32, 45, 80, 100, 123, 128, 179, 180, 702/183, 187–189, 193; 700/72, 73; 710/56, 710/57
See application file for complete search history.

(56) References Cited

U.S. PATENT DOCUMENTS

| | | | |
|---|---|---|---|
| 4,019,174 A | | 4/1977 | Vanderpool et al. |
| 4,091,367 A | * | 5/1978 | Harman .................... 340/552 |
| 4,293,221 A | * | 10/1981 | Kay et al. .................. 356/318 |
| 4,338,950 A | | 7/1982 | Barlow, Jr. et al. |
| 4,478,088 A | | 10/1984 | Loveland |

(Continued)

OTHER PUBLICATIONS

Shapiro, Practical Flow Cytometry, 3rd Ed., Alan R. Liss, Inc. 1985.

*Primary Examiner*—Marc S. Hoff
*Assistant Examiner*—Manuel L Barbee
(74) *Attorney, Agent, or Firm*—Charles D. Huston; Ann Marie Mewherter; Daffer McDaniel, LLP

(57) ABSTRACT

A method and apparatus for providing a zero dead time for flow analyzers, flow cytometers, and other measurement devices. A circular buffer is used to store data from a flow analyzer in a plurality of data storage areas, until it is convenient to implement more time-consuming data processing procedures. User specified parameters, including sampling rate and/or sampling period, size and number of data storage areas, size of the circular or other buffer, signal-to-noise threshold, order of processing when a plurality of Digital Signal Processors (DSPs) is used, and fixed trailing distance, are used to provide flexible and convenient operation by a user. The probability of missing a rare event occurring within the laser beam or other light beam of a flow analyzer or other measurement device is reduced to zero. Functional equivalents may be used in place of the circular buffer, for example, First In-First Out buffers which route data to a cache for potential re reading and/or reprocessing or additional processing of data, cascading buffers, etc.

21 Claims, 4 Drawing Sheets

U.S. PATENT DOCUMENTS

| | | |
|---|---|---|
| 4,661,913 A | 4/1987 | Wu et al. |
| 5,091,951 A | 2/1992 | Ida et al. |
| 5,150,313 A * | 9/1992 | van den Engh et al. ...... 702/79 |
| 5,250,856 A * | 10/1993 | Burton et al. ................ 326/110 |
| 5,278,988 A | 1/1994 | Dejean et al. |
| 5,299,141 A | 3/1994 | Hungerford et al. |
| 5,325,509 A * | 6/1994 | Lautzenheiser ............. 711/137 |
| 5,367,474 A * | 11/1994 | Auer et al. ................... 702/21 |
| 5,448,706 A | 9/1995 | Fleming et al. |
| 5,550,058 A | 8/1996 | Corio et al. |
| 5,556,764 A * | 9/1996 | Sizto et al. ................. 435/7.24 |
| 5,734,422 A | 3/1998 | Maurer et al. |
| 5,745,793 A | 4/1998 | Atsatt et al. |
| 5,880,474 A | 3/1999 | Norton et al. |
| 5,909,278 A | 6/1999 | Deka et al. |
| 6,064,439 A | 5/2000 | Kimura et al. |
| 6,148,365 A | 11/2000 | Buer |
| 6,285,377 B1 * | 9/2001 | Greenbaum et al. ........ 345/441 |
| 6,411,904 B1 * | 6/2002 | Chandler ..................... 702/21 |

* cited by examiner

ZERO DEAD TIME ARCHITECTURE AND METHOD FOR FLOW CYTOMETER

CROSS REFERENCE TO RELATED APPLICATIONS

This Application is a Continuation of U.S. Utility application Ser. No. 10/140,943, filed May 9, 2002 now U.S. Pat. No. 6,658,357, which is a Continuation of U.S. Utility application Ser. No. 09/310,755, filed May 13, 1999 (issued as U.S. Pat. No. 6,411,904), and claims priority to U.S. Provisional Application No. 60/085,415, filed May 14, 1998, and U.S. Provisional Application No. 60/085,381, filed May 14, 1998, all of which are hereby incorporated by reference in their entireties.

FIELD OF THE INVENTION

The present invention relates generally to an apparatus for, and a method of, increasing the quantity of information obtained from flow analyzers or other data collection devices by temporarily storing data relating to, for example, particles, cells, and inter-event background noise from flow through an examination zone. In particular, the present invention relates to an apparatus for and a method of achieving zero dead time by temporarily storing such data in a circular buffer, or similar buffer or temporary storage capability, for later processing.

BACKGROUND OF THE INVENTION

Flow cytometry is used conveniently to measure quickly one or more optical parameters of the cells and/or particles that pass through a light beam that impinges on a narrow examination zone. Background information on flow cytometry is found, for example, in Shapiro's *Practical Flow Cytometry*, Third Edition (Alan R. Liss, Inc. 1995), incorporated herein by reference in its entirety.

In conventional flow cytometers, sample fluid containing sample cells and/or particles is introduced from a sample tube into or near the center of a faster flowing stream of sheath fluid, which draws the sample toward the center of the combined streams. This process, known a hydrodynamic focusing, allows the cells and/or particles to be delivered reproducibly to the center of the measuring point in the flow cell or other examination zone. Typically, the cells and/or particles are in suspension in the flow cell.

A continuous wave laser focuses a laser beam on the cells and/or particles as they pass through the examination zone in a flow stream of the suspension. When an object of interest in the flow stream is struck by the laser beam, certain signals result and are sensed by detectors. For example, these signals include forward light scatter intensity, which provides information concerning the size of individual cells and/or particles, and side light scatter intensity, which provides information regarding the relative size and refractive properties of individual cells and/or particles.

Other signals which may be sensed by detectors include fluorescence emissions from one or more fluorescent dyes and/or other fluorescent molecules; for example, tryptophan, or other fluorescent amino acid(s) or other molecule(s), that is native to a protein or other peptide, or to another biomolecule or man-made molecule. Typically, when a plurality of different fluorescing molecules is employed in an analytical scheme, fluorescence emission peaks are selected so as to minimize or, ideally, eliminate spectral overlap between the respective fluorescence emission peaks.

For example, ideally, fluorescence emission peaks will differ by 50 nm, though lesser (or larger) spectral separation also can be accommodated and used to advantage, for example, 20, 30 or 40 nm, where the greater the spectral separation, the more powerful is the discrimination between the respective fluorescence emitters. In addition, quantum efficiency is considered in the choice of fluorescent molecules. In the case of use of a plurality of different fluorescent molecules, a separate detector is tuned to and used for the different wavelength of emission of each fluorescence emitter. The excitation wavelength for more than one fluorescent molecule can be the same, or different excitation wavelengths can be used to match the excitation spectrum of each different fluorescent molecule.

The optical signals that are generated by an analytical procedure are transmitted to an output meter(s) and/or data storage means. Signal processing, for example, by a Digital Signal Processor or DSP, can be employed before and/or after intensity data on the measured optical signals are transmitted to the output meter(s) and/or data storage means.

In flow cytometry, an "event" occurs when a cell or particle passes through the beam of the laser or other light source. As the event progresses, the light measured from scattering and/or fluorescence emission increases as the cell or particle enters the beam, reaches a maximum at the center of the beam, and tapers to a nominal value as it leaves the beam.

State of the art flow cytometers commonly use one of two systems to measure events. One system uses peak detectors, including peak hold circuits, to sustain the maximum signal level obtained from an event, and to measure optical parameters relating to cells and/or particles passing through a laser beam. Once a peak detector has sensed and measured an event, the peak detectors are turned off to provide sufficient time for an analog to digital, or A/D, converter to digitize that maximum value of the signal. During the time that the peak detectors are off, termed "dead time", any event occurring within the laser beam will go undetected.

The second system uses an integrator to measure the area under the peak collected for an event. With either system, when an event occurs within the cytometer's light beam during the dead time, the event will go undetected.

Normally, such lack of detection of an event does not constitute a significant problem because, for a large number of events, only a tiny number will be missed. However, applications which require the detection of rare, critical events, for example, identification of one special cell or particle in a thousand or a million, suffer from the possible non-detection of a rare event when current generation flow cytometers are used for detection and measurement. The higher the throughput, the greater is the probability that such a critical event will be missed per unit time period.

One solution to problems encountered in sorting samples in flow cytometry is provided by U.S. Pat. No. 5,550,058 to Corio, et al., incorporated herein by reference. *Corio, et al.* provides a means of flexibly controlling decisions on the sorting of events detected in a flow cytometer. Events are pre-qualified according to user-selectable parameters to permit reduction of events missed during dead time. However, the *Corio, et al* reference does not teach or suggest a means of reducing the probability of missing a dead time event to zero.

Thus, it would be beneficial in the art of flow analyzers, including flow cytometers or other analyzing equipment, to have a means to reduce to zero the probability of missing any event, including a rare, dead time event.

It is also desirable to provide efficiently and inexpensively a system and/or method for reducing the probability of missing an event.

It is further desirable to provide efficiently and inexpensively a system and/or method for reducing the probability of missing an event for high sampling rates, for example, on the order of approximately a sampling period, such as one sample per millisecond or shorter period.

SUMMARY OF THE INVENTION

Accordingly, it is a feature and advantage of the present invention to provide an apparatus and a method for reducing the dead time to zero in flow analyzers, flow cytometers, and other measurement devices.

It is another feature and advantage of the present invention to provide a means to reduce the dead time to zero in flow analyzers, flow cytometers, and other measurement devices by use of, for example, a circular buffer to store optical data until the data can be processed by at least one digital signal processor or other processor.

It is a further feature and advantage of the present invention to provide a means to reduce the dead time to zero in flow analyzers, flow cytometers, and other measurement devices by providing software that permits the user to specify one or more of data collection, data storage, and data processing parameters, such as size of data storage areas, number of data storage areas, sampling rate (and/or the inverse: length of sampling or sample period), signal-to-noise (S/N) threshold, and fixed trailing distance.

It is a feature and advantage of the present invention to provide efficiently and inexpensively a system and/or method of reducing the probability of missing an event.

It is another feature and advantage of the present invention to provide efficiently and inexpensively a system and/or method of reducing the probability of missing an event in the presence of a high sampling rate.

It is yet another feature and advantage of the instant invention to provide the capability of enhancing data analytical capability by going back in time to re-examine and reprocess data in "old" data storage areas in order, potentially, to recreate a more complete event peak(s) by applying special algorithms to subthreshold data.

The instant invention provides an apparatus and a method of use of that apparatus to reduce dead time to zero or substantially zero in a measurement device. The apparatus includes 1) a circular buffer that has a) a plurality of data storage areas that are linked to receive and consecutively store incoming data from a plurality of successive sampling periods of a measurement device that measures events occurring in a measurement zone, b) a First Pointer (or first logical pointer), and c) a Second Pointer (or second logical pointer); and 2) at least one Digital Signal Processor (DSP) or other data processor.

Each data storage area is configured to receive and store data from one sampling period. Furthermore, the data storage areas are linked in an order that provides storage for data from a next-in-time sampling period into the next-in-order data storage area. The First Pointer directs receipt and storage of data of the next-in-time sampling period into the next-in-order data storage area; and, once all data storage areas contain data, the First Pointer directs receipt of data of the next-in-time sampling period, and storage by overwriting therewith the data in the next-in-order data storage area, which contains the oldest data of the circular buffer.

The Second Pointer is directed to the data storage area that stores data from a sample period preceding the current time by at least a fixed trailing distance, referenced to the First Pointer; and the Second Pointer directs one of the at least one DSPs to read and process data in the data storage area to which the Second Pointer is directed.

Once the next-in-time data from the current sampling period have been stored, the First Pointer advances to the next-in-order data storage area. In addition, once data in the data storage area to which the Second Pointer is directed have been processed, the Second Pointer advances to the next-in-order data storage area to repeat the cycle of data processing, followed by advancement to the next-in-order data storage area.

Other addressable buffers can alternatively be used where the addressable range of data allows the system to go forward and sufficiently backward to obtain previously collected samples. For example, a FIFO and backward cache combination can alternatively be used in the present invention, as can a cascading buffer.

The method of the instant invention entails applying the above apparatus to collect and process data from events occurring in a measurement device, particularly a measurement device with a flowcell, such as a flow cytometer or other flow analyzer.

The fixed trailing distance is set by the user to equal the longest possible time for an event, or longer, often falling in the 10 to 100 millisecond range. The size and number of data storage areas in the circular buffer also are user specified. Data storage areas often are set to 12 to 16 bits, though larger and smaller sizes may be used to adjust for particular applications. The number of data storage areas often is set to about one thousand, or greater. However, numbers of data storage areas less than a thousand also can be used advantageously.

The sampling rate, and/or its inverse which is length of sampling period, also are user specified. A typical sampling rate is one million per second, which equates to sampling periods of one microsecond each. However, larger and smaller figures can be utilized according to the particular application.

When a plurality of DSPs is used, the user may specify the order of use of the respective DSPs. For example, one DSP can control storage of data incoming to the circular buffer, and one or a plurality of DSPs can handle processing of the data, as directed by the Second Pointer.

Buffers that are functionally equivalent to circular buffers also can be used, for example, a First In-First Out buffer which temporarily stores data (or lack thereof) from the respective data storage areas into one or more caches for possible later processing; double or triple cascading buffers; etc.

In another embodiment, an FPGA (Field Programmable Gate Array) may be programmed as a state machine, for example, with four or five states, to replace use of a DSP for inputting data into the circular buffer or functional equivalent. In a further embodiment, the present invention contemplates a data collection and measurement device collecting data with substantially zero dead time, comprising: a) a circular buffer comprising a plurality of data storage areas that are linked to receive and consecutively store incoming data from a plurality of successive sampling periods for at least one event of a measurement device, where each data storage area is configured to receive and store data from one sampling period, and the data storage areas are linked in an order that provides storage for data from a next-in-time sampling period into the next-in-order data storage area; b) a First Pointer; c) a Second Pointer; and d) at least one Digital Signal Processor (DSP), where the First Pointer directs receipt and storage of data of the next-in-time sampling period into the next-in-order data storage area, and, once all data storage areas contain data, directs receipt of data of the next-in-time sampling period, and storage by overwriting therewith data in the next-in-order data storage area, the Second Pointer is directed to the data storage area that stores data from a sample period preceding a current time of data receipt and storage by a fixed trailing distance as referenced to the First Pointer, and directs one of the at least one DSPs to read and process data in the data storage area to which the Second Pointer is directed, and wherein once the next-in-time data have been stored, the First Pointer advances to the next-in-order data storage area, and once data in the data storage area to which the Second Pointer is directed have been processed, the Second Pointer advances to the next-in-order data storage area; wherein said collection and measurement device collects and processes data from at least one event; and wherein the fixed trailing distance equals at least a longest possible time for an event. A preferred embodiment provides that the fixed trailing distance is about 10 to about 100 milliseconds.

Another embodiment of the present invention provides a flow analyzer collecting data with substantially zero dead time for at least one event, comprising: at least one buffer having a plurality of data storage areas that are adapted to receive and store incoming data from a plurality of sampling periods for the at least one event collected by said flow analyzer, said at least one buffer including previously stored data from a sample period preceding a current time of the receipt and the storage of the data and including an addressable range of the plurality of data storage areas to go sufficiently backward in the plurality of sampling periods; and at least one processor connected to said at least one buffer, receiving the data from the at least one of the plurality of data storage areas of said at least one buffer, and said flow analyzer collecting and processing the data from the at least one event with substantially zero dead time by reading from said at least one buffer the previously stored data from the sampling period preceding the current time of the plurality of sampling periods. In a preferred embodiment, the flow analyzer is a flow cytometer.

An even further embodiment of the present invention provides a flow analyzer collecting data with substantially zero dead time for at least one event, comprising: at least one buffer means for having a plurality of data storage areas that are adapted to receive and store incoming data from a plurality of sampling periods for the at least one event collected by said flow analyzer, said at least one buffer means for including previously stored data from a sample period preceding a current time of the receipt and the storage of the data and including an addressable range of the plurality of data storage areas to go sufficiently backward in the plurality of sampling periods; and at least one processor for receiving the data from the at least one of the plurality of data storage areas of said at least one buffer means, said flow analyzer collecting and processing the data from the at least one event with substantially zero dead time by reading from said at least one buffer means the previously stored data from the sampling period preceding the current time of the plurality of sampling periods. In a preferred embodiment, the flow analyzer is a flow cytometer.

The above broad outline of the more important features of the instant invention has been presented 1) to facilitate understanding of the following sections which provide greater detail with respect to components of the instant invention, and 2) to highlight succinctly contributions of the instant invention to the art. However, it is to be understood that the above outline, as well as the terminology and details as to construction, arrangement and practice of the instant invention presented in the following sections, are exemplary and not limiting; i.e., the instant invention is capable of other embodiments as to construction, arrangement and practice.

As such, those skilled in the art will appreciate that the conception, upon which this disclosure is based, can readily be utilized as a basis for designing other structures and methods of practice to execute the purposes of the instant invention. Therefore, it is important that the instant disclosure and claims be regarded as embracing equivalent constructions and practices insofar as they do not depart from the spirit and scope of the invention as disclosed herein.

Another purpose for this SUMMARY OF THE INVENTION section is to enable the U.S. Patent Office and the public generally, including scientists, engineers and practitioner in the art who are not familiar with patent or legal terms or phraseology herein, to determine quickly the nature and essence of the instant disclosure with only cursory review. Thus, the intention of this section is not to limit the scope of the instant invention in any way.

For a more complete understanding of the instant invention, including its operating advantages and various uses, reference should be made to the following drawings, descriptive matter, and claims, which illustrate preferred embodiments of the invention.

DESCRIPTION OF THE PREFERRED EMBODIMENTS

Figure 1:
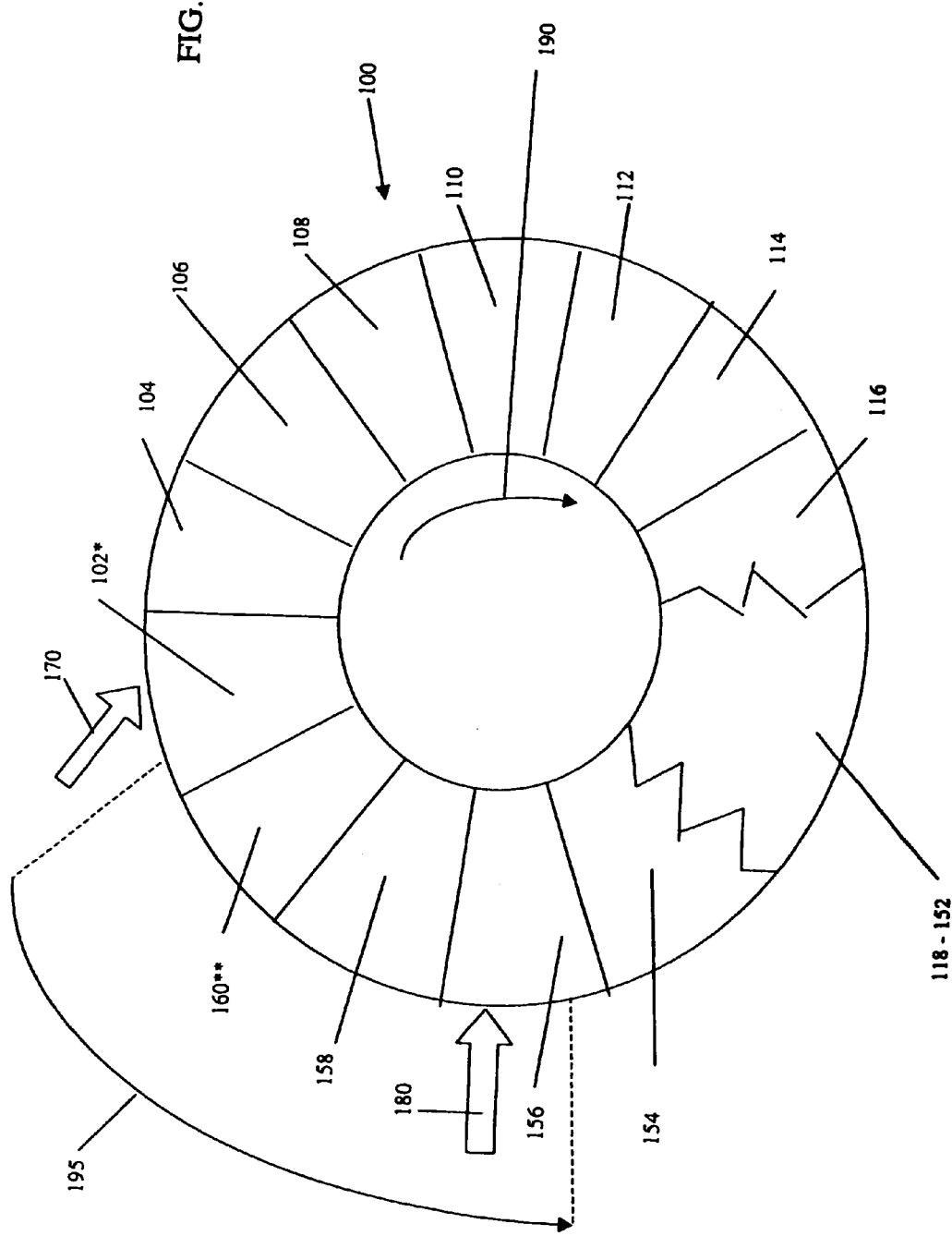
FIG. 1 is an embodiment of a circular buffer according to the instant invention.

The present invention provides a system and method of reducing the dead time to zero or substantially zero in flow analyzers, flow cytometers, and other measurement devices. Advantageously, the present invention provides the user the ability to specify one or more data collection, data storage, and data processing parameters, such as size of data storage areas, number of data storage areas, sampling rate (and/or the inverse: length of sampling or sample period), signal-to-noise (S/N) threshold, and fixed trailing distance.

Each data storage area is configured to receive and store data from, for example, one or more sampling periods. The data storage areas are optionally linked in an order that provides storage for data from a next-in-time sampling period into the next-in-order data storage area. A First Pointer (or first logical pointer) directs receipt and storage of data of the next-in-time sampling period into the next-in-order data storage area. Once all data storage areas contain data, the First Pointer directs receipt of data of the next-in-time sampling period, and storage by overwriting therewith the data in the next-in-order data storage area, which contain the oldest data of the buffer, such as a standard circular buffer.

A Second Pointer (or second logical pointer) is directed to the data storage area that stores data from a sample period preceding the current time by at least a fixed or predetermined trailing distance with reference, for example, to the First Pointer or other reference. The Second Pointer directs at least one digital signal processor (DSP) or other data processor to read and process data in the data storage area to which the Second Pointer is directed.

Once the next-in-time data from the current sampling period have been stored, the First Pointer advances to the next-in-order data storage area. In addition, once data in the data storage area to which the Second Pointer is directed have been processed, the Second Pointer advances to the next-in-order data storage area to repeat the cycle of data processing, followed by advancement to the next-in-order data storage area.

The present invention is based, in part, on the discovery that samples containing important data were being lost in data collection of analyzing equipment, such as flow analyzers or cytometers. As a result, the overall accuracy of the cytometer was questionable or could be improved. Accordingly, having realized that important samples were being lost for certain applications described above, it was determined that an addressable buffer having the capability of obtaining a predetermined amount of data backward in time would improve the overall accuracy and efficiency of the flow analyzer or cytometer.

Other addressable buffers can alternatively be used where the addressable range of data allows the system to go forward and sufficiently backward to obtain previously collected samples. For example, a FIFO and backward cache combination can alternatively be used in the present invention, as can a cascading buffer. The number of samples for which the buffer need go backward in time varies, depending on the application, but may be anywhere from 1 sample, 20 samples, and higher.

Referring to FIG. 1, an embodiment of a circular buffer (also referred to as a "circular buffer means" or "circular memory structure") 100 having 30 data storage areas is presented. The 30 data storage areas are represented by consecutive even numbers 102 through 160. First Pointer (or first logical pointer) 170 indicates the data storage area to which the next data sample from the next sample period is to be stored by, for example, overwriting the existing data (if any) when the next data sample is transmitted from a flow analyzer, flow cytometer, or other measurement device to circular buffer 100.

First Pointer 170 is directed to data storage area 102, which, at this particular instant in time, holds the oldest data of the circular buffer, as is indicated by a single asterisk. When data are transmitted to circular storage buffer at the beginning of an analytical procedure, instead of overwriting old data, new data are added consecutively to the data storage areas of circular buffer 100, thus creating a series of linked next-in-time data storage areas.

Circular arrow 190 indicates the forward-in-time direction of advancement both for data acquisition and usual data processing (i.e., not back-in-time processing). Thus, data storage area 104 holds the second oldest data at this instant in time, 106 holds the third oldest data, etc., to data storage area 160, which holds the newest data, as is indicated by a double asterisk. The next set of incoming data from a sample period will overwrite the old data of 102.

Just prior to the arrival of the next set of incoming data transmitted to circular buffer 100 from the next sample period, First Pointer 170 advances to data storage area 104, to direct overwriting of the (now) oldest data consecutively for each data storage area, thus continuously advancing in the forward-in-time direction of circular arrow 190. This process continuously creates and updates a series of next-in-order data storage areas that store next-in-time data.

Referring again to FIG. 1, Second Pointer (or second logical pointer) 180 is shown as being directed to data storage area 156 of circular buffer 100. Second Pointer 180 indicates the current data storage area whose data are to be read next and processed by, for example, a DSP or other processor (not shown in the figure) if the data reach a user specified threshold signal-to-noise (S/N) ratio. After the DSP reads the data stored in data storage area 156, Second Pointer 180 advances in the direction of arrow 190 to data storage area 158, and so forth in sequence. As indicated above, other buffer devices may be used that are addressable; therefore, there is no requirement that the above operations necessarily be performed sequentially or in a specific linear manner or order.

The number of data storage areas in a circular buffer or other buffer is flexibly specified by the user to be as large or as small as the requirements of the particular application. For example, a thousand data storage areas provide sufficient means to store one thousand sampling periods, where each sampling period is one microsecond. Circular buffer 100 can comprise more than or less than 1,000 data storage areas; and the length of time of a sampling period can be greater than or less than one millisecond (i.e., the sampling rate can be less than or greater than one million per second).

Similarly, the size of the data storage areas is defined by the user or is user-selectable in concert with the requirements of the particular application. For example, a capacity of 12–16 bits per data storage area will suffice for some applications, whereas more than 20 bits will be required in other applications, such as complex and/or high amplitude fluorescence emission or other peaks.

Practice of the present invention does not require a one-to-one (i.e., in locked-step) direct correspondence between the quantity of data read and processed by the DSP (or the time required therefor), as directed by Second Pointer 180, and the quantity of incoming data that overwrites the oldest data (or the time required therefor), as directed by First Pointer 170. For example, First Pointer 170 advances in steady cadence in step with the sampling rate, for example, one million per second. When data in a data storage area do not meet the user specified S/N threshold, Second Pointer 180 also moves in cadence with the sampling rate.

On the other hand, when data in a data storage area do meet a user specified S/N threshold and thus indicate an event in progress, Second Pointer 180 advances quickly to the next-in-order data storage area. As long as the data in a data storage area do not meet the user specified S/N threshold, a minimum, fixed lag time $\tau$ or fixed trailing distance is maintained relative to First Pointer 170, which lag time must be at least equal to $\tau_{mc1}$ the longest time for an event. Thus, the fixed trailing distance serves as a minimum lag time criterion when data in a data storage area do not meet the S/N threshold.

In other words, $\tau$ is the user defined lag time between the current transmission of data from a sampling period to circular buffer 100, and the reading by the DSP of insufficient S/N data stored $\tau$ seconds previously. Thus, the DSP is programmed to examine data collected from a point back in time $\tau$, which is equal to or greater than $\tau_{mc1}$ measured from the time that First Pointer 170 is directed to the data storage area into which the next set of incoming data (from the next sampling period) are to be stored.

Stated differently, when First Pointer 170 advances to the next-in-order data storage area, Second Pointer 180 also advances to the next data storage area if data in the preceding data storage area did not meet the S/N threshold. However, if those data did reach the S/N ratio, then Second Pointer 180 advances rapidly ahead to permit the DSP to read and process the data of that storage area forward in time, as well as to read and processes the data of subsequent next-in-order data storage areas relating to the event. Thus, when an event is detected, Second Pointer 180 advances in the direction of circular arrow, 190 to the next-in-order data storage area with the next-in-time data for the event. In so doing, Second Pointer 180 will "overrun" fixed lag time τ, but will not overrun First Pointer 170 because is at least equal to the longest possible event.

Alternative embodiments can employ a plurality of DSPs or other standard processors to increase processing efficiency as Second Pointer 180 advances rapidly to process an event. With such a plurality of DSPs, the user can specify their order of processing as Second Pointer 180 advances through the series of data storage areas with data from the event.

In addition, more sophisticated standard protocols or other standard protocols can be employed for determining whether data in a given data storage area belong to a peak from an event. For example, when each set of data in a series of data storage areas does not meet the user specified S/N threshold, but the values of each set of data from the series of data storage areas are monotonically increasing or otherwise substantially increasing by a user specified amount, and/or within a few data storage areas the increasing sets of data mature into a peak or other recognizable event, then Second Pointer 180 retreats to the first-in-order data storage area with data now deemed (by virtue of the logic programmed into the software therefor) consistent with the occurrence of an event. Therefore, the data of such a series of data storage areas are thereby processed as being part of a peak of an event.

This is the reason for the requirement of having a "circular buffer" or a functional equivalent; i.e., a means to reexamine previous data in view of data subsequent in time that confirm the presence of an event. Thus, this embodiment provides powerful additional analytical power over prior art flow analyzers and other measurement devices.

The term circular buffer (and other equivalent expressions, such as "circular buffer means" and "circular memory structure") refers to a memory structure or device comprising data storage areas that are linked or related in a prescribed order in a fashion that permits a number of functional capabilities. One functional capability comprises the capability of ordered or predetermined filling (for example, next-in-time or other addressable fashion) of those data storage areas with consecutive packets of data. Alternatively, or in addition, another functional capability is to store data and permit the data to be output in a predetermined manner, while also allowing a predetermined amount of back or past data to be retrieved therefrom.

Once all of the discrete number of data storage areas each have a packet of data, a second cycle of ordered filling commences with the next-in-time data overwriting the data in the data storage area having the oldest data, and so forth for all subsequent cycles, where each cycle transmits consecutive data packets into data storage areas in the same order or in the same addressable fashion as the previous cycle.

A second functional capability is that of permitting a pointer (for example, Second Pointer 180) to go back in time and reexamine data in view of subsequent data, per one or more user specified criteria. In addition, it is important to recognize that other buffer structures (whether presently available or developed in the future) that accomplish results that are functionally equivalent to those described herein above, as required by the instant invention, are encompassed by the instant invention.

Two non-limiting examples can be mentioned: 1) cascading double or triple buffers, and/or 2) First In-First Out buffers which are coupled with at least one cache to which data from each respective data storage area are transferred when Second Pointer 180 advances to the next data storage area. In addition, any other buffer exhibiting the above two functional capabilities are hereby explicitly encompassed by the instant invention.

Figure 2:
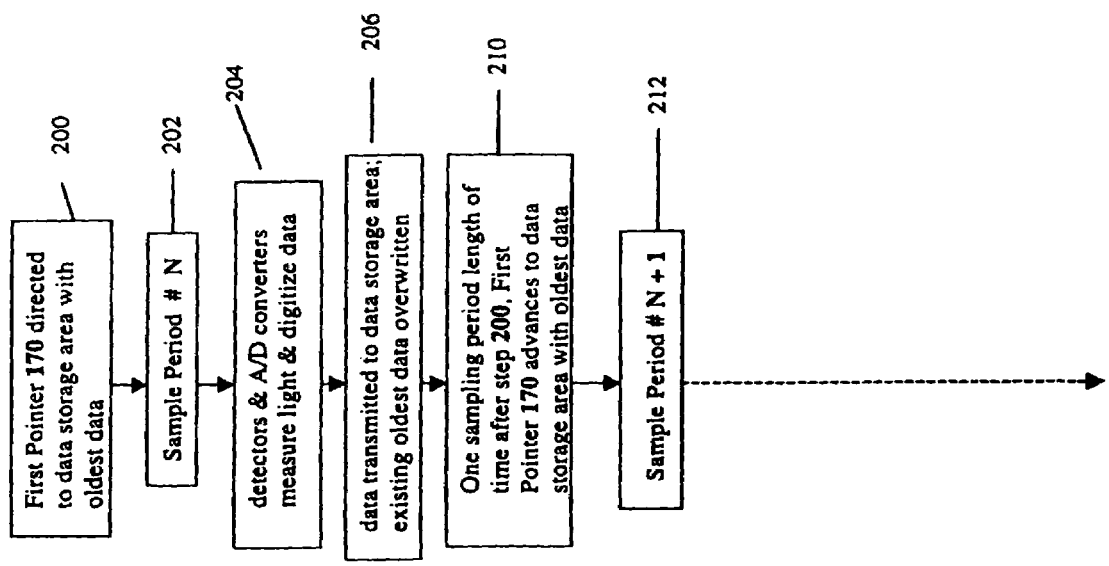
FIG. 2 is a flow chart of an embodiment for writing data from a flow analyzer to the circular buffer of FIG. 1.

Referring to FIG. 2, the processing logic of data transfer to circular buffer 100 of FIG. 1 is shown. Step 200 shows that First Pointer 170 is directed to the storage area of circular buffer 100 having the oldest data. Sample Period N then occurs 202, and sensors sample and measure light parameters, and high speed analog to digital (A/D) converters digitize the data 204. Digitized data from the sensors are then transmitted 206 to the data storage area to which First Pointer 170 is directed, and the oldest data are overwritten. When the length of a sample period (inverse of the sampling frequency) has passed, measured from the position of First Pointer 170 at step 200, First Pointer 170 advances 210 to the next-in-order data storage area or predetermined data storage area, which has the next-in-time data, which now are the oldest data in the circular buffer; and the cycle (equivalent to the sequential combination of steps 204, 206, and 210) continues, beginning with the next sampling period N+1 (212).

In the case of an analytical process that is just starting, the equivalent of steps 200–206 will apply, though the data storage areas initially will be empty, because there are no data to be overwritten. For example, if, the sampling rate is one million per second, and if there are one thousand data storage areas, such a state of empty data storage areas will exist for substantially only one thousandth of a second.

For purposes of analysis, an event is defined by the user with respect to a minimum datum criterion, for example, when the signal-to-noise (S/N) ratio is equal to a threshold value of about 2 or 3, or other threshold value. The S/N threshold value may be increased or decreased to compensate for the degree of purity of the samples (for example, whether integrity of the particles is high, or many of the particles have crumbled into smaller entities) and/or the purity of the fluid, or to compensate for any other situation (for example, bubbles) affecting background noise in the cytometric or other flow measurement readings, or in readings from any other measurement device.

In effect, the S/N threshold may be adjusted to reflect the range of anticipated small signal amplitudes, particularly including amplitudes of background signals. As is indicated above in the discussion of FIG. 1, more sophisticated S/N threshold strategies can be employed when the application will benefit.

The rate of sampling also is selected by the user, for example, one million sampling periods per second, or smaller or greater. Typically, a fixed rate of oversampling is used that creates about 8–12 sampling periods per average event, with a maximum of about 20 sampling moments per event. However, greater or lesser values may be used according to a particular application; for example, when there is a complex or broad, multi-peak fluorescence emission spectrum, more than 50 or 100 sampling periods per event can be specified advantageously.

Figure 3:
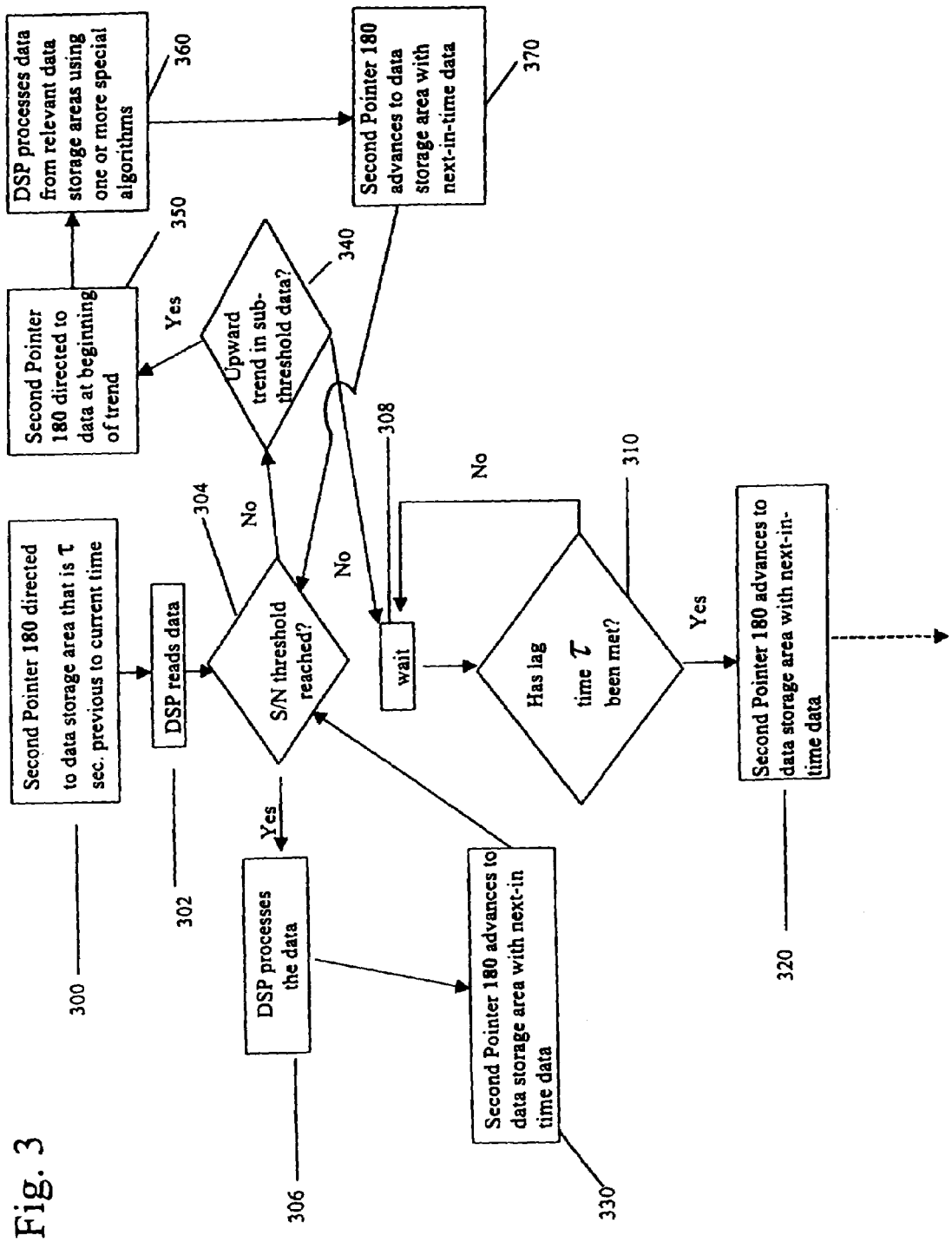
FIG. 3 is a flow chart of an embodiment for reading and processing data from the circular buffer of FIG. 1.

Referring now to FIG. 3, at times not distant from the measuring, transmitting, and storing of new data, as outlined by consecutive steps 200, 202, 204, 206, and 210 of FIG. 2, data processing occurs with respect to data stored elsewhere in circular buffer 100, starting with step 300. At step 300, Second Pointer 180 is directed to the data storage area that stores data collected no less than τ sec. previously, which period of time is also referred to as the "fixed trailing distance." The DSP then reads the data 302, and determines 304 whether the data reach the user selected S/N threshold so as to warrant processing 306 by the DSP.

If the S/N ratio threshold has been reached, the data in that data storage area are processed 306, Second Pointer 180 advances to the next-in-order data storage area 330, and a determination is made as to whether the data in that storage area reach the S/N threshold 304.

On the other hand, if the S/N ratio threshold has not been reached by the data in the particular data storage area, then more sophisticated standard analytical strategies are employed, such as asking if there is an upward trend in consecutive subthreshold data 340. If the answer is "yes," then Second Pointer 180 goes back to data at the beginning of the trend 350, and processes the data in the series of consecutive data storage areas that constitute the "trend" 360. Subsequently, Second Pointer 180 advances to the data storage area with the next-in-time data 370, and the cycle begins again with the question "Has the S/N threshold been reached" 304.

Alternative or additional algorithms can be employed at steps 340 and/or 360. For example, a "small signal detector algorithm" that facilitates inter-processor (for example, inter-DSP) communication with respect to data that do not meet the S/N threshold. For example, when a plurality of DSPs is employed, such an algorithm will direct each of the plurality of DSPs to cooperatively go back in time to preceding data that, individually or collectively, may constitute a portion of an event peak that is developing. Likewise, such an algorithm also can be employed for the "end" portion of an event peak. In effect, this kind of algorithm signals the need for additional scrutiny by one or more analytical programs that can include, for example, fitting and/or smoothing and/or rounding and/or other programs that provide a basis for additional signal processing.

On the other hand, if there is no upward trend in subthreshold data (or if any other user specified criterion applies, such as length of an event), then a pause or wait 308 is made. Next, the question "Has lag time τ been met?" is posed 310; i.e., were the data in the data storage area collected and stored no less than τ sec. previous to current time, as measured relative to first Pointer 170? If the answer is "No," a further wait 308 is imposed, and cycling back to the question of step 310 is performed. If the answer is "Yes," Second Pointer 180 then advances 320 to the next-in-order data storage area that has the next-in-time data. The particular data storage area to be examined next is always the one with data stored from the sampling period immediately following the sampling period just examined, i.e., next-in-time (see direction of circular arrow 190 in FIG. 1). Subsequently, a new cycle of data reading and processing commences.

A number of such cycles of collecting and processing of data can occur before the next event occurs. For example, if there are one million sampling periods per second (i.e., the sampling rate), and if 20,000 cells and/or particles ("events") are read per second, which is the fastest rate currently commercially available, then the average eventless time between samples is about 40 milliseconds if 10 sampling periods are required to collect the data of a single event. When circular buffer 100 is selected to have one thousand data storage areas, then data in those thousand data storage areas represent sampling over a period of one thousandth of a second.

Thus, the average eventless time of about 40 milliseconds translates into an average of about 40 sampling periods with no detectable data until the next event. Calculation also shows that, at a given instant in time, a circular buffer with 1,000 data storage areas will have data from about 20 events [1,000 milliseconds/(10 milliseconds event length+40 milliseconds eventless time)]. Data storage areas holding data for inter-event periods are filled with background noise data.

In a preferred embodiment, simultaneous data samples (for example, from a single sampling period) from each of a plurality of channels of data that have been detected and digitized are stored in a single data storage area. For example, a detector for one channel will collect and transmit data on scattered excitation light; a detector for a second channel will collect and transmit data on fluorescence emission data of a first fluorescent dye; a detector from a third channel will collect and transmit data on fluorescence emission from a second fluorescent dye; and all of these data are stored in or on a single data storage area.

A larger number of data storage areas may be employed for simultaneous data from a multitude of channels, with order of processing being specified by the user. For example, three channels can be used to collect emission data from three spectrally distinct fluorescent dyes; one channel can collect forward scattered light; one channel can collect side scattered light; and the order for processing data from the five channels is specified by the user. Alternatively, five separate data storage areas can be used respectively to store data from the five channels, where the order of storage is user specified.

In another embodiment, more than one DSP can be employed to work in concert with Second Pointer 180 as a solution to the problem that processing activities often take considerable time. For example, time consuming digital filtering (for example, standard finite impulse response filtering, or "FIR") can be used, and/or any of various waveform analysis procedures that are often employed to improve the quality of data extracted in the presence of noise. When more than one DSP is so employed, the user specifies the order of processing by the respective DSPs or other processors. For example, a first DSP processes data of the next-in-order data storage area, a second DSP processes data of the (now) next-in-order data storage area, and so forth. Other configurations are also possible in accordance with the present invention.

It is beneficial that the present invention permits the user to specify not only the S/N threshold, but also optionally the order of transmission and processing of multiple channels of data from events, the order of processing when there are multiple DSPs, the size of a data storage area, the number of data storage areas and/or the total size of circular buffer. Thus, in instances of complex emission peaks, multiple data inputs, or any other complicated data stream, the user can readily adapt the data storage parameters and other parameters to fit the current use, thus ensuring efficient processing and ample data storage capacity to accommodate at least the largest possible quantity of data resulting from one or more events occurring in close time proximity.

In a preferred embodiment, circular buffer 100 has 1,000 or more data storage areas that each hold all incoming data from two or more channels (or three or more in complex analytical applications). A typical minimum configuration includes one channel collecting scattered light from excitation light, a second channel collecting fluorescence emission light from a first fluorescent dye, and a third channel collecting fluorescence emission light from a second fluorescent dye. However, depending on the application, as few as one channel or as many as five or more channels can provide the incoming data to circular buffer 100. The upper limit of channels is immaterial to the present invention, but more than five channels clearly is within the scope of the present invention.

Figure 4:
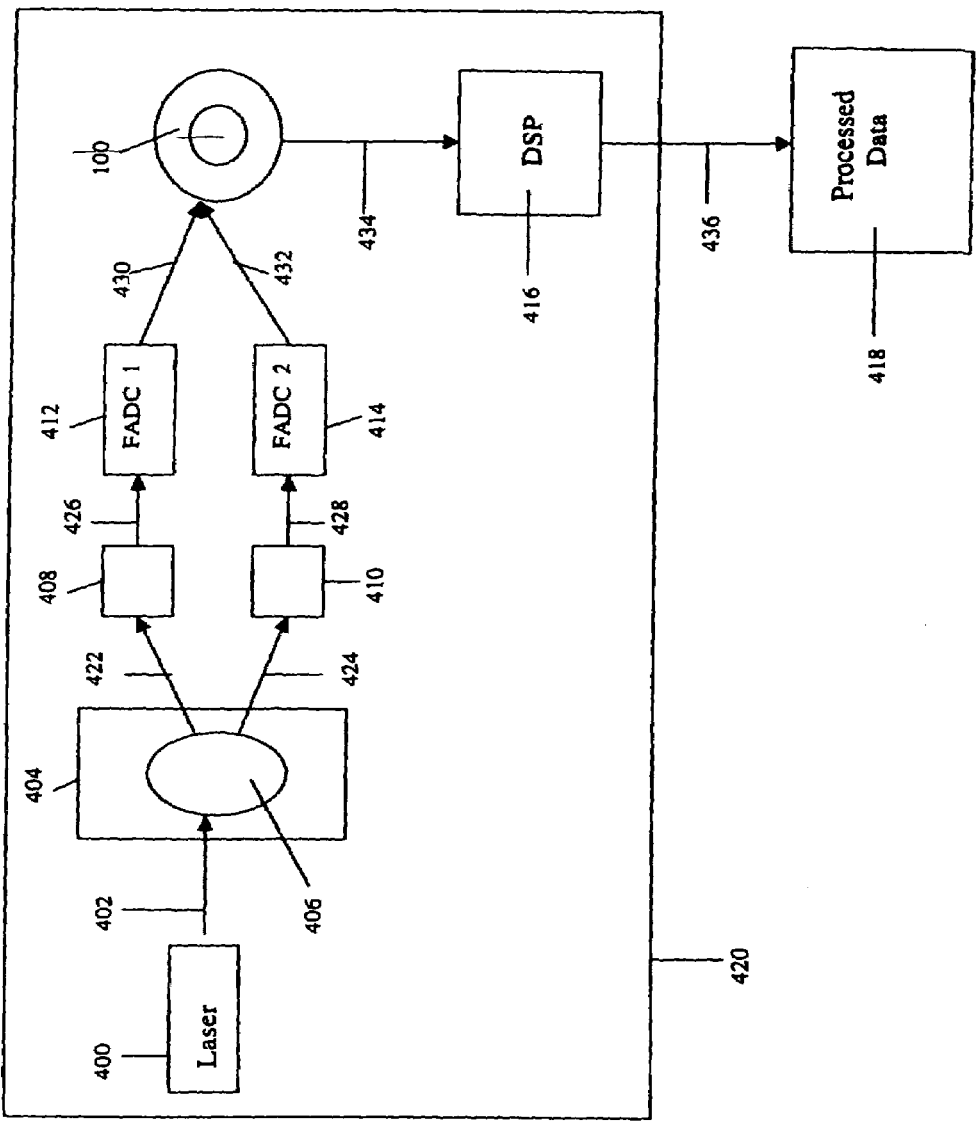
FIG. 4 is a schematic showing the functioning of a circular buffer within a flow analyzer.

Referring to FIG. 4, a schematic is shown for functioning of circular buffer 100 within a flow analyzer 420, for example, a flow cytometer. Laser light beam 402 from laser 400 is shown to impinge on a particle 406 as it passes through examination zone 404 of a flow cuvette. Light 422, 424 that is scattered, emitted (for example, fluorescence emission), refracted, or otherwise produced is then sensed by one or more detectors 408, 410, which then transmit their data 426, 428 to their respective FADC (filtering, amplification, and digital conversion) units 412, 414. The FADCs then transmit 430, 432, their respective resulting digitized data to circular buffer 100. By the processes described herein above, circular buffer 100 then transmits 434 data meeting the user specified S/N threshold to a DSP or other data processor 416 for final data processing. Results of processing by the DSP or other processor 416 are then output 436 as the final, processed data 418. It is important to recognize that circular buffer 100 may comprise a part of DSP or other processor 416, or be operatively coupled thereto.

Also, it is important to recognize that other buffers can be used in place of circular buffer 100, and yet fulfill the accomplishments described herein above with respect to circular buffer 100, for example, cascading buffers, and First In-First Out buffers which utilize a cache for re-reading and/or reprocessing data when so directed by Second Pointer 180.

The present invention is directed to use with flow cytometers, flow analyzers, other flow measurement devices, etc. The processing logic of the present invention that, in effect, permits digitized signals to be stored rapidly, and thereafter be processed by at least one DSP or other processor (using eventless time periods to conduct the time consuming procedures of signal processing), can be applied equally well to other measurement applications.

Attached hereto as part of the instant Specification in the APPENDIX is a copy of an assembly language program that implements one embodiment of the present invention.

What is claimed is:

1. A system configured to collect data with substantially zero dead time, comprising:
   a flow analyzer configured to collect data for events in successive sampling periods with substantially zero dead time between the successive sampling periods;
   at least one buffer having a plurality of data storage areas, wherein the at least one buffer is adapted to receive the data from said flow analyzer and to store the data for each of the successive sampling periods in different data storage areas with substantially zero dead time between storage of the data in the different data storage areas, and wherein said at least one buffer comprises an addressable range of the plurality of data storage areas to go sufficiently backward in the successive sampling periods; and
   at least one processor connected to said at least one buffer, wherein the at least one processor is adapted to receive and process the data from the plurality of data storage areas of said at least one buffer, and wherein the at least one processor is further adapted to process the data from the plurality of data storage areas at a rate that is determined based on a signal-to-noise ratio or value of the data from the plurality of data storage areas.

2. The system of claim 1, where the flow analyzer is a flow cylometer.

3. A system configured to collect data with substantially zero dead time, comprising:
   a flow analyzer configured to collect data for events in successive sampling periods with substantially zero dead time between the successive sampling periods;
   at least one buffer means for having a plurality of data storage areas, wherein the at least one buffer means is adapted to receive the data from the flow analyzer and to store the data for each of the successive sampling periods in different data storage areas with substantially zero dead time between storage of the data in the different data storage areas, and wherein said at least one buffer means comprises an addressable range of the plurality of data storage areas to go sufficiently backward in the successive sampling periods; and
   at least one processor adapted to receive and process the data from the plurality of data storage areas of said at least one buffer means, wherein the at least one processor is further adapted to process the data from the plurality of data storage areas at a rate that is determined based on a signal-to-noise ratio or value of data from the plurality of data storage areas.

4. The system of claim 3, where the flow analyzer is a flow cytometer.

5. A system configured to collect data with substantially zero dead time, comprising:
   a flow analyzer configured to collect data during successive sampling periods with substantially zero dead time between the successive sampling periods;
   an addressable buffer comprising data storage areas, wherein the addressable buffer is configured to store the data for each of the successive sampling periods in different data storage areas with substantially zero dead time between storage of the data in the different data storage areas; and
   a processor configured to process the data in the different data storage areas at a rate that is determined based on a signal-to-noise ratio or value of the data in the different data storage areas.

6. The system of claim 5, wherein the rate is different than a rate at which the data is stored in the different data storage areas.

7. The system of claim 5, wherein the processor is further configured to process the data in the different data storage areas after the data has been stored in the different data storage areas for a time longer than a longest possible time for an event.

8. The system of claim 5, wherein the addressable buffer further comprises a number of the data storage areas such that a predetermined amount of the data backward in time is available for re-processing by the processor.

9. The system of claim 5, wherein the addressable buffer is a circular buffer.

10. The system of claim 5, wherein the addressable buffer is a cascading buffer.

11. The system of claim 5, wherein the addressable buffer is a First In-First Out buffer coupled to a backward cache.

12. The system of claim 5, wherein one or more parameters of the flow analyzer, the addressable buffer, the processor, or some combination thereof are user specified.

13. The system of claim 5, wherein the data storage areas are linked in an order such that the data for the successive sampling periods is stored in the data storage areas in the order in which the data storage areas are linked.

14. The system of claim 5, further comprising a pointer configured to direct the storage of the data in the addressable buffer.

15. The system of claim 5, further comprising an additional processor configured to direct the storage of the data in the addressable buffer.

16. The system of claim 5, further comprising a field programmable gate array configured to direct the storage of the data in the addressable buffer.

17. The system of claim 5, further comprising a pointer configured to direct processing of the data by the processor.

18. The system of claim 5, further comprising an additional processor configured to process the data in the different data storage areas.

19. The system of claim 5, wherein the processor is further configured to process the data stored in a series of the different data storage areas as being part of one event.

20. The system of claim 5, wherein the data for each of the successive sampling periods comprises data from a plurality of channels of the flow analyzer.

21. A method for collecting data with substantially zero dead time, comprising:

collecting data with a flow analyzer during successive sampling periods with substantially zero dead time between the successive sampling periods;

storing the data for each of the successive sampling periods in different data storage areas with substantially zero dead time between storage of the data in the different data storage areas; and processing the data in the different data storage areas at a rate that is determined based on a signal-to-noise ratio or value of the data in the different data storage areas.

* * * * *

UNITED STATES PATENT AND TRADEMARK OFFICE
CERTIFICATE OF CORRECTION

| | |
|---|---|
| PATENT NO. | : 7,047,138 B2 |
| APPLICATION NO. | : 10/694086 |
| DATED | : May 16, 2006 |
| INVENTOR(S) | : Chandler |

Page 1 of 1

It is certified that error appears in the above-identified patent and that said Letters Patent is hereby corrected as shown below:

IN THE CLAIMS:

Col. 14, line 4: Please delete "cylometer" and substitute --cytometer--.

Signed and Sealed this

Seventeenth Day of April, 2007

JON W. DUDAS
*Director of the United States Patent and Trademark Office*